(12) United States Patent
Sugimura et al.

(10) Patent No.: US 8,292,696 B2
(45) Date of Patent: Oct. 23, 2012

(54) METHOD OF MANUFACTURING MICRONEEDLE

(75) Inventors: Hiroshi Sugimura, Tokyo (JP); Gaku Suzuki, Tokyo (JP); Masahiro Ueno, Tokyo (JP); Yoshihiro Kodama, Tokyo (JP); Takao Tomono, Tokyo (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 156 days.

(21) Appl. No.: 12/662,397

(22) Filed: Apr. 14, 2010

(65) Prior Publication Data

US 2010/0198169 A1    Aug. 5, 2010

Related U.S. Application Data

(63) Continuation of application No. 12/320,493, filed on Jan. 27, 2009, now Pat. No. 7,789,733, which is a continuation of application No. PCT/JP2007/064809, filed on Jul. 27, 2007.

(30) Foreign Application Priority Data

Jul. 27, 2006    (JP) ................................. 2006-204417
Nov. 15, 2006    (JP) ................................. 2006-308877

(51) Int. Cl.
    *B24B 9/00*    (2006.01)
(52) U.S. Cl. .......................................... 451/28; 451/58
(58) Field of Classification Search .................. 451/57, 451/58, 41, 44, 28, 182, 541; 125/13.01
    See application file for complete search history.

(56) References Cited

U.S. PATENT DOCUMENTS

| 6,183,434 | B1 | 2/2001 | Eppstein |
| 6,451,240 | B1* | 9/2002 | Sherman et al. ............... 264/504 |
| 6,503,231 | B1* | 1/2003 | Prausnitz et al. ............. 604/272 |
| 7,578,954 | B2* | 8/2009 | Gartstein et al. .............. 264/154 |
| 2002/0177858 | A1* | 11/2002 | Sherman et al. ............... 606/131 |

FOREIGN PATENT DOCUMENTS

| JP | 1-271178 | 10/1989 |
| JP | 2000-126934 | 5/2000 |
| JP | 2002-369816 | 12/2002 |
| JP | 2004-58265 | 2/2004 |
| JP | 2004-516868 | 6/2004 |
| JP | 2005-21677 | 1/2005 |
| JP | 2005-503194 | 2/2005 |
| JP | 2006-513811 | 4/2006 |
| WO | 02/100474 A2 | 12/2002 |

OTHER PUBLICATIONS

U.S. Appl. No. 12/320,493, filed Jan. 27, 2009, Hiroshi Sugimura et al., Toppan Printing Co., Ltd.
International Search Report for PCT/JP2007/064809, mailed Oct. 23, 2007.
English Translation of the International Preliminary Report on Patentability issued Feb. 5, 2009 in corresponding International Patent Application PCT/JP2007/064809.

(Continued)

*Primary Examiner* — Robert Rose

(57) ABSTRACT

A method of manufacturing a microneedle including the steps of forming a plurality of first linear grooves on a substrate in parallel to one another along a first direction using grinding, and forming a plurality of second linear grooves on the substrate in parallel to one another in a second direction intersecting the first direction using grinding.

7 Claims, 15 Drawing Sheets

OTHER PUBLICATIONS

Office Action mailed from the Unites States Patent and Trademark Office on Dec. 4, 2009 in the related U.S. Appl. No. 12/320,493.
Office Action mailed from the Japanese Patent Office on Apr. 5, 2011 in the corresponding Japanese patent application No. 2009-184189.

Office Action mailed from the U.S. Patent and Trademark Office on Dec. 4, 2009 in the related U.S. Appl. No. 12/320,493.
Notice of Allowance mailed from the U.S. Patent and Trademark Office on Jun. 7, 2010 in the related U.S. Appl. No. 12/320,493.

* cited by examiner

A > B

F I G. 11A
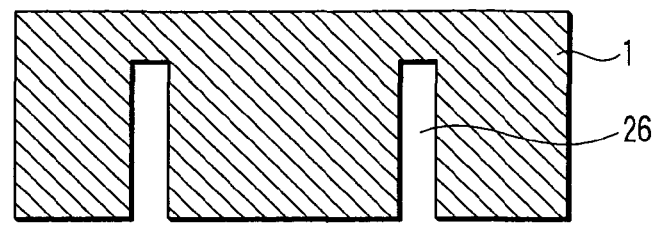
F I G. 11B
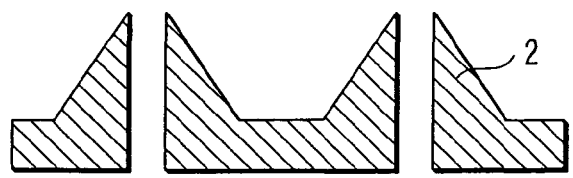
F I G. 12A
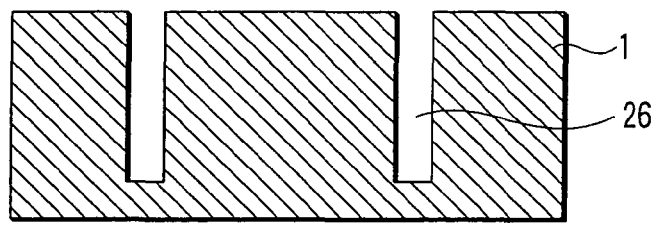
F I G. 12B
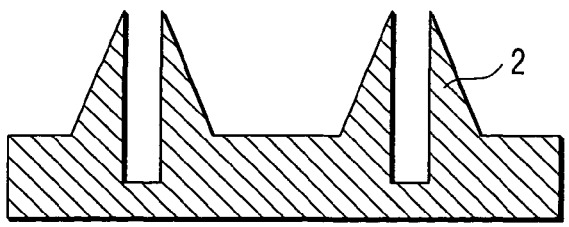

F I G. 13A
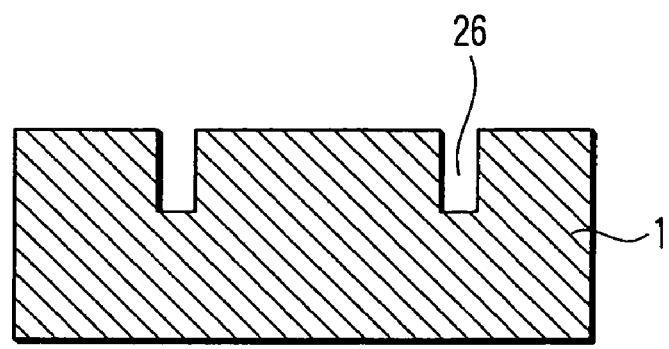
F I G. 13B
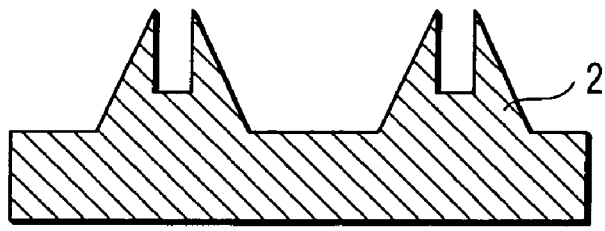

F I G. 14A 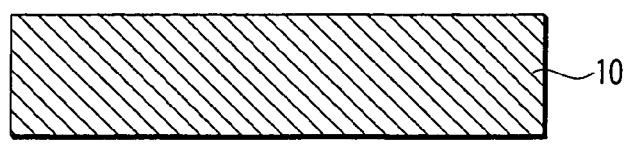
F I G. 14B 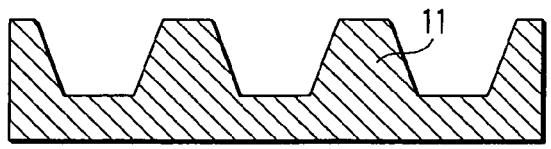
F I G. 14C 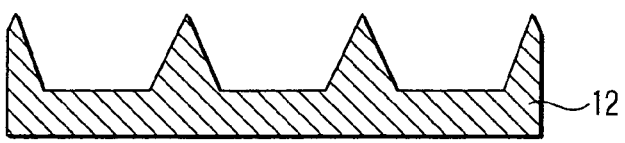
F I G. 14D 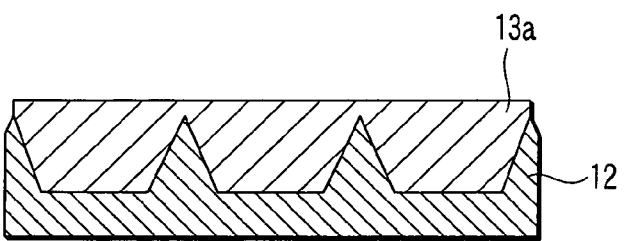
F I G. 14E 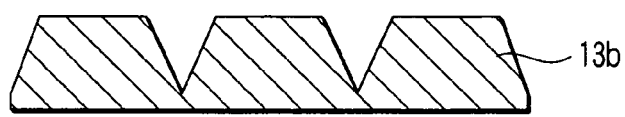
F I G. 14F 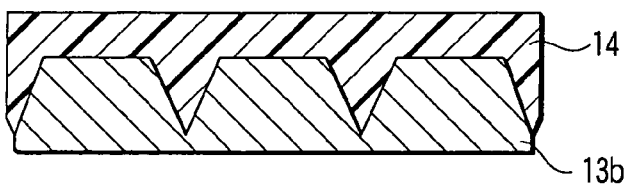
F I G. 14G 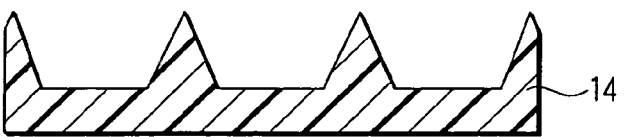

F I G. 18A
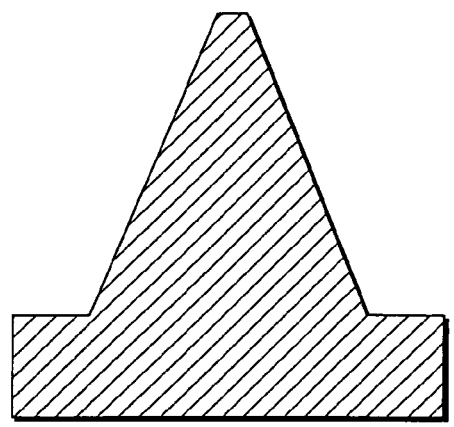
F I G. 18B
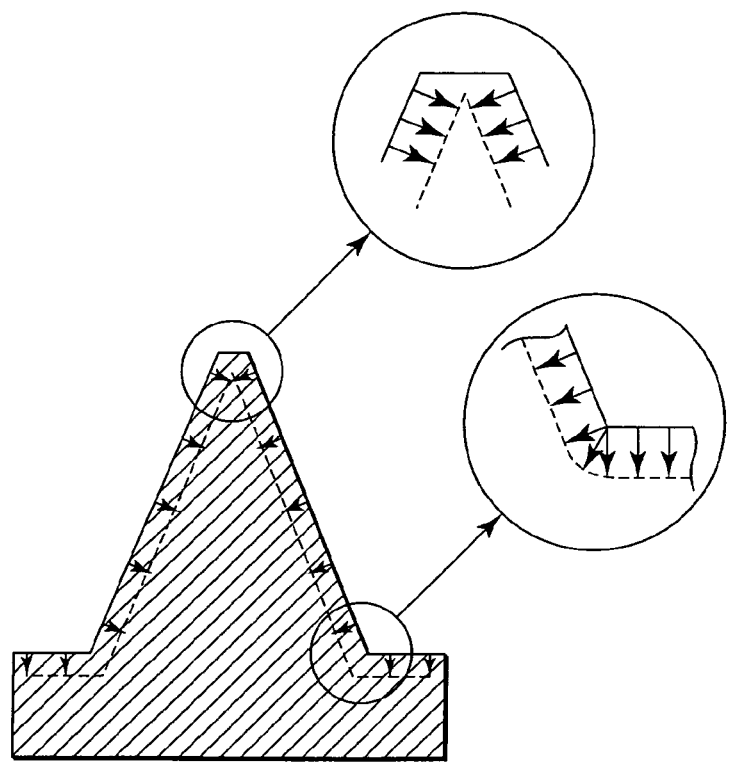
F I G. 18C
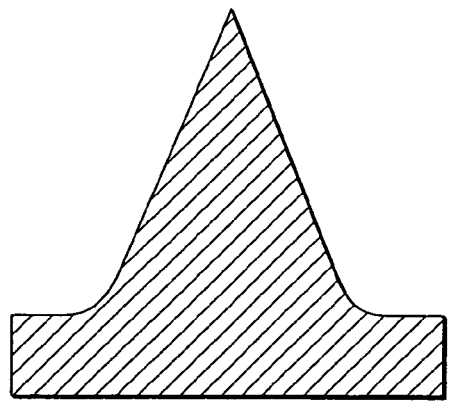

METHOD OF MANUFACTURING MICRONEEDLE

CROSS-REFERENCE TO RELATED APPLICATIONS

This application is a continuation of U.S. application Ser. No. 12/320,493, filed Jan. 27, 2009 now U.S. Pat. No. 7,789,733, which is a continuation application of PCT Application No. PCT/JP2007/064809, filed Jul. 27, 2007, which application in turn is based upon and claims the benefit of priority from prior Japanese Patent Applications No. 2006-204417, filed Jul. 27, 2006 and No. 2006-308877, filed Nov. 15, 2006, the entire contents of which are incorporated herein by reference.

BACKGROUND

1. Field

The present invention relates to a method of manufacturing a microneedle.

2. Description of the Related Art

Percutaneous absorption has been known as one of the methods for administering a drug by permitting it to permeate through the skin. This method is noninvasive, and makes it possible to simply administer the drug without giving pain to the human body. However, administration by percutaneous absorption may be difficult depending on the kind of the drug.

Accordingly, a noticed method is to directly inject the drug beneath the skin by perforating the skin using a microneedle array having many needles of micron order in order to permit the drug to be efficiently absorbed into the body. This method enables simple subcutaneous administration without using any special devices (see U.S. Pat. No. 6,183,434).

The microneedle is required to have sufficient fineness and point angle for piercing the skin, and a sufficient length for permitting the drug solution to be permeated under the skin. The diameter of the needle is desirably in the range of several μm to several hundred μm. The needle desirably has a length enough for penetrating the corneal layer as the outermost layer of the skin. While the thickness of the corneal layer differs depending on the site of the body, it is about 20 μm on average. The epidermis is laid under the corneal layer with a thickness of about 200 μm to about 350 μm, and the dermic layer in which capillary vessels are extended is laid under the epidermis. Accordingly, at least 20 μm or more of the length of the needle is necessary for allowing the needle to penetrate the corneal layer in order to permit the drug solution to permeate. A needle length of at least 350 μm or more is necessary for sampling the blood.

Usually, the microneedle has been attempted to be manufactured by processing silicon. Silicon is a material widely used for manufacturing MEMS devices and semiconductors, and is cheap and excellent in fine processability. A method proposed for manufacturing a silicon microneedle includes the steps of: patterning a silicon oxide film formed on both surfaces of a silicon wafer; applying crystal anisotropy etching from the surface of the wafer; and applying isotropic etching from the back surface of the wafer. For example, a microneedle with a length of 500 μm or more and a width of 200 μm or less may be manufactured by this method. Sampling of the blood is further secured by forming an array of such microneedles (see Jpn. Pat. Appln. KOKAI Publication No. 2002-369816). Likewise, another proposed manufacturing method includes the steps of: subjecting a silicon substrate to wet etching; and forming the microneedle by taking advantage of a difference in the etching rate among crystal orientations of a silicon single crystal material (see Jpn. Pat. Appln. KOKAI Publication No. 2004-58265).

Methods for manufacturing the microneedle using materials other than silicon have been also proposed. For example, the microneedles are formed by a wire cutting method on one surface of a processed steel plate. The size and shape of the microneedle formed are controlled by changing downward and upward cutting angles (see Jpn. PCT National Publication No. 2006-513811).

The material constituting the microneedle is required to be harmless to the human body even when the microneedle is broken and left behind in the body. Examples of the material that is considered to be promising include a biocompatible material such as a medical silicone resin, maltose, polylactic acid and dextran (see Jpn. Pat. Appln. KOKAI Publication No. 2005-21677).

A transcription molding method represented by injection molding, imprinting and casting is effective for manufacturing these fine structures with a low cost in large scale. However, since a master plate having an inversed shape of desired recessed and projected portions is necessary for molding by any of these methods, the manufacturing process becomes quite complicated for forming a structure having a high aspect ratio (the ratio of height or depth to width of the structure) and a sharp tip as the microneedle.

Since the method using wet etching in the related art takes advantage of a difference in etching rates among orientations of the crystal plane, a highly purified single crystal material is necessary for manufacturing the microneedle. The taper angle and point angle of the microneedle is determined by the property of the single crystal material. Accordingly, it is difficult to manufacture the microneedle by designing an appropriate shape and size of the microneedle while taking the constitution of the skin into consideration.

Since it is impossible to shift upward cutting to downward cutting immediately after upward cutting has reached the apex of the microneedle in the method using wire cutting, horizontal cutting actually advances for a length from 1 to 20 μm. Consequently, the microneedle manufactured has a trapezoidal cone shape having a flat plane on the apex of the needle, and the performance for piercing with the microneedle is impaired.

Generally, columnar or conical needles are aligned upright on the surface of the flat substrate in the microneedle aligned in an array. However, the side surface of the microneedle becomes to have a sharp corner with the surface of the substrate at the base of the microneedle in the manufacturing method in the related art. A stress is converged on the corner portion at the base of the microneedle when the microneedle is shaped as described above, and the microneedle may be broken by piercing.

SUMMARY

An object of the invention is to provide a method of manufacturing a conical microneedle having a desired length with a sharp tip.

The present invention provides a method of manufacturing a microneedle comprising the steps of: forming a plurality of first linear grooves in parallel to one another along a first direction on a substrate using grinding; and forming a plurality of second linear grooves in parallel to one another along a second direction intersecting the first direction on the substrate using grinding.

In the invention, grinding moving in a horizontal direction on the surface of the substrate may be applied plural times relative to one linear groove when forming the linear grooves.

In the invention, the first linear groove and second linear groove may be sequentially formed to one another when forming the first linear grooves and second linear grooves.

In the invention, preferably, a dicing blade is used for grinding, the dicing blade has a side surface, a tip surface and an inclined surface between the side surface and tip surface, and a boundary between the inclined surface and tip surface is chamfered.

In the invention, a dicing blade may be used for grinding, the dicing blade may be moved so that the inclined surfaces partially overlap when forming adjoining two first linear grooves, and the dicing blade may be moved so that the inclined surfaces partially overlap when forming adjoining two second linear grooves.

In the invention, an island structure may be formed by the steps including: forming a plurality of first linear grooves in parallel to one another along a first direction on a substrate by using grinding; and forming a plurality of second linear grooves in parallel to one another along a second direction intersecting the first direction on the substrate by using grinding, and the island structure may be subjected to isotropic etching.

In the invention, a dicing blade may be used for dicing as grinding, and further linear grooves corresponding to the first and/or second linear grooves may be formed on the substrate by using dicing blades having different angles of the inclined surface.

In the invention, the first linear groove intersects the second linear groove with an angle of, for example, 90°.

The invention may include a step for forming a plurality of third linear grooves in parallel to one another along a third direction that intersects the first direction and second direction. Two of the first, second and third linear grooves intersect with an angle of, for example, 120°.

In the invention, a non-penetrated hole or a penetrated hole may be provided on the substrate, and the microneedle may be formed at a position displaced from the position of the non-penetrated hole or penetrated hole.

In the invention, the non-penetrated hole or penetrated hole may be provided on the substrate, and the microneedle may be formed so as to overlap the position of the non-penetrated hole or penetrated hole.

The invention also provides a method of manufacturing a microneedle including: using the microneedle manufactured by the above-mentioned method of manufacturing a microneedle as a master plate; manufacturing a replication plate from the master plate; and manufacturing the microneedle by transcription from the replication plate. The replication plate is preferably transcribed onto a biocompatible material upon transcription from the replication plate.

The invention also provides a microneedle manufactured by any one of the above-mentioned methods for manufacturing a microneedle.

The invention provides an apparatus for manufacturing a microneedle having a dicing blade including a side surface, a tip surface and an inclined surface between the side surface and tip surface.

According to the method of manufacturing a microneedle of one embodiment of the invention, grooves are formed by grinding, and the top of the sharp portion of the microneedle is formed by the overlap of the inclined surfaces. Accordingly, the sharp portion of the microneedle is not flattened unlike in the microneedle manufactured by wire cutting. Since the microneedles may be manufactured in every column by providing linear grooves, the microneedles may be collectively formed particularly when microneedles are aligned in an array. A conical microneedle having a variety of shapes of the basal plane may be manufactured by controlling the shape of the groove and the angle formed by intersection between the grooves. For example, a microneedle having a rectangular basal plane may be manufactured by permitting the first linear groove to intersect the second linear groove at an angle of 90°.

According to the method of manufacturing a microneedle of the invention, a microneedle having a gentle slope at the base may be manufactured by using a chamfered dicing blade so that the tip surface does not intersect the inclined surface with a sharp corner. This permits the stress converged at the base upon piercing to be relaxed, and consequently a microneedle having a shape suitable for suppressing the microneedle from being broken upon piercing may be manufactured.

According to the method of manufacturing a microneedle of another embodiment of the invention, the tip of the microneedle may be formed sharp without restricting the material of the substrate to a material made of a single crystal material by using groove processing with a dicing blade and isotropic etching together. The shape of the microneedle may be controlled by the shape of the groove. Consequently, a microneedle having a high freedom of design of the taper angle and point angle may be manufactured with a sharp tip.

The shape of the microneedle may be transcribed to various materials by using the microneedle manufactured as described above as a master plate for manufacturing a replicate plate, and by manufacturing the microneedle by transcription from the replication plate. Consequently, a microneedle using a material that gives low burden to the body may be manufactured by transcribing the needle, for example, onto a biocompatible material (such as medical silicone resin, maltose, polylactic acid and dextran). The production cost may be reduced while the productivity is improved since a lot of microneedles can be manufactured from the same replication plate that has been manufactured from a material having a high mechanical strength.

BRIEF DESCRIPTION OF THE DRAWINGS

FIGS. 11A and 11B show cross-sectional views illustrating a method of manufacturing a microneedle according to the invention.

FIGS. 12A and 12B show cross-sectional views illustrating a method of manufacturing a microneedle according to the invention.

FIGS. 13A and 13B show cross-sectional views illustrating a method of manufacturing a microneedle according to the invention.

FIGS. 14A to 14G show cross-sectional views illustrating a method of manufacturing a microneedle according to the invention.

FIGS. 18A to 18C show cross-sectional views of shape modification of the microneedle by applying isotropic etching.

DETAILED DESCRIPTION OF EMBODIMENTS

A microneedle is manufactured by processing a substrate using grinding in the method of manufacturing a microneedle according to the invention. The "grinding" as used herein refers to a processing method by which a processing object is ground with hard and fine abrasive grains constituting a grinding stone that is rotated at high speed. For example, a dicing blade may be used as the grinding stone.

Liner grooves may be formed on a substrate to be processed using the dicing blade attached at the top of a spindle that is rotating at a high speed in the grinding of the invention. The dicing blade is formed at the periphery of a disk-shaped support. The material of the dicing blade desirably has high hardness, and diamond abrasive grains are used in many cases. A diamond wheel having the dicing blade containing diamond abrasive grains on the entire surface of the periphery of the disk-shaped support may be used in the invention. The diamond wheel is widely used in a cutting process of a substrate in the semiconductor industry, and is a cheap and readily available material.

Figure 1A:
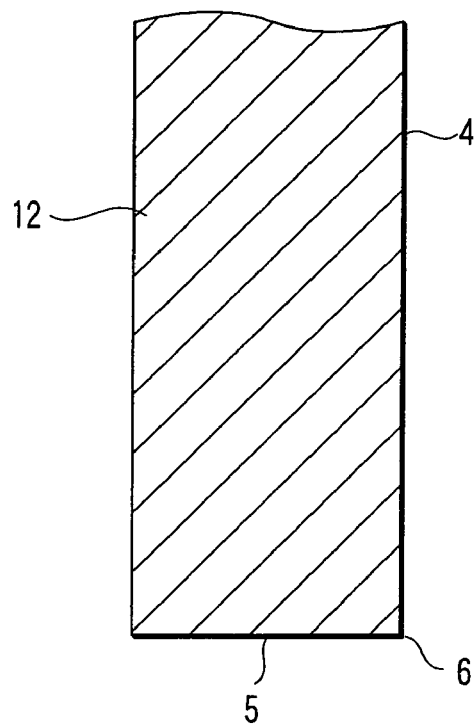
FIGS. 1A and 1B show cross-sectional views of examples of the top of the dicing blade.
Figure 1B:
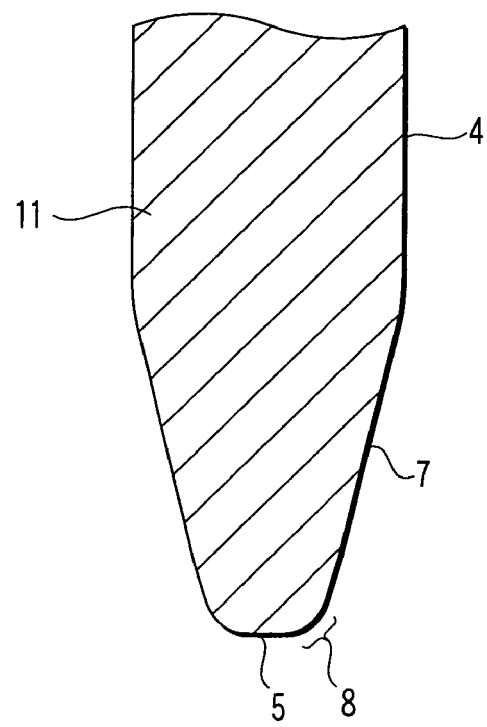

FIGS. 1A and 1B show partial cross-sectional views of the tip of the dicing blade. As shown in FIG. 1A, the cross sectional shape of a dicing blade 12 usually has a crossing angle of 90° between a side surface 4 and a tip surface 5 to form an apex 6. On the contrary, a dicing blade 11 used for manufacturing the microneedle of the invention has side surfaces 4, tip surface 5 and inclined surfaces 7 formed between the side surfaces and tip surface as shown in FIG. 1B. The angle of inclination of the inclined surface 7 determines the angle of the sidewall of the finally formed microneedle. Accordingly, the angle of the sidewall of the microneedle manufactured may be controlled by the inclined surface of the dicing blade.

The boundary between the tip surface 5 and inclined surface 7 of the dicing blade 11 is desirably chamfered so that the surfaces do not cross to one another with a distinct angle at the boundary. FIG. 1B shows a cross-sectional view of the dicing blade 11 that is processed into a shape having a chamfered surface 8 at around the apex formed by intersection of the inclined surface 7 and tip surface 5. The chamfered surface 8 determines the shape of the base of the finally formed microneedle. In other words, a microneedle having a gentle slope at the base may be manufactured by providing the chamfered surface 8. This permits the stress converged at the bottom of the microneedle upon piercing may be relaxed, so that a microneedle having a shape suitable for suppressing the microneedle from being broken upon piercing may be manufactured. While the method for processing the tip of the dicing blade is not particularly limited, polishing with a grinding stone may be favorably used.

An example of a method of manufacturing a microneedle according to the invention will be described below with reference to FIGS. 2A to 2F.

<Process for Providing a First Linear Groove on the Substrate>

Figure 2A:
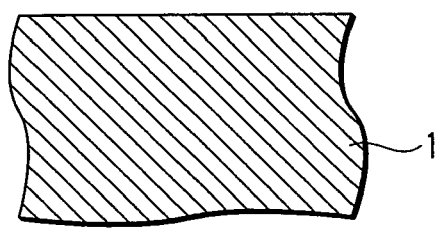
FIGS. 2A to 2F show cross-sectional views illustrating a method of manufacturing a microneedle according to the invention.

A substrate 1 is prepared as shown in FIG. 2A. The material of the substrate 1 is not particularly limited, and is desirably selected in terms of processability and availability. Specific examples of the material include ceramics such as alumina, aluminum nitride and machinable ceramics; crystalline materials such as silicon, silicon carbide and quartz; organic materials such as acrylic resins and polyacetal; metallic materials such as nickel and aluminum; and glass.

Figure 2B:
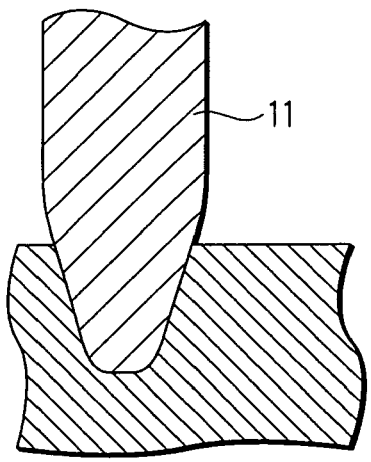

Then, the surface of the substrate 1 is subjected to dicing as shown in FIG. 2B while the dicing blade 11 is rotated to form a first linear groove with a given length. The first linear groove may be formed not always in a straight line but also in a curved line. A polygonal microneedle having a basal plane closed with a curve may be manufactured when the first linear groove is provided as a curved line. The grinding condition such as the rotation speed and grinding speed of the dicing blade is not particularly limited, and the processing conditions are desirably optimized by taking the materials of the dicing blade 11 and substrate 1 into consideration.

Figure 2C:
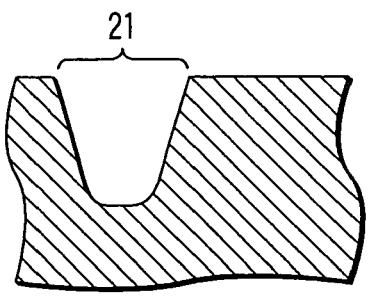

The first linear groove 21 is formed by dicing as shown in FIG. 2C. The slope of the side surface of the first linear groove 21 matches the slope of the inclined surface 7 formed at the tip of the dicing blade 11 as shown in FIG. 1B. Likewise, the portion where the side surface of the first linear groove 21 intersects the basal plane thereof has a shape with a slope corresponding to the chamfered surface 8 formed at the tip of the dicing blade 11 as shown in FIG. 1B.

<Process for Forming Other First Linear Groove>

Figure 2D:
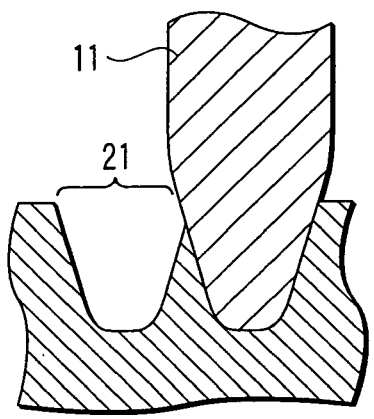
Figure 2E:
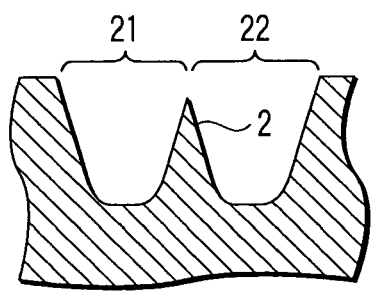

Another first linear groove 22 is formed so that the groove does not intersect the above-mentioned first linear groove 21 and is adjoining in parallel to the latter linear groove. One or more other first linear grooves are formed. As shown in FIG. 2D, another first linear groove 22 is formed adjacent to the first linear groove 21 with the dicing blade 11. At this time, the dicing blade 11 is desirably moved so as to have an overlap portion at a part of the inclined surface of the first linear groove 21. This permits a microneedle being excellent in piercing ability to be manufactured by avoiding the sharp tip of the needle from being flattened. The first linear groove 22 is diced in parallel to the first linear groove 21. Consequently, the adjoining first linear groove 22 is formed as shown in FIG. 2E. Since an apex of the top portion is formed by the overlapping between the inclined surface 7 of the dicing blade 11 used for forming the first linear groove 21 and the inclined surface 7 of the dicing blade 11 used for forming the first linear groove 22, a needle 2 having a sharp apex is formed. Accordingly, the first linear grooves are formed so that they are adjoining to one another when plural first linear grooves are provided.

The height of the needle 2 is determined by the depth of dicing, the angle of the inclined surface 7 at the tip of the dicing blade 11, and the overlap distance between the first linear groove 21 and first linear groove 22.

Figure 2F:
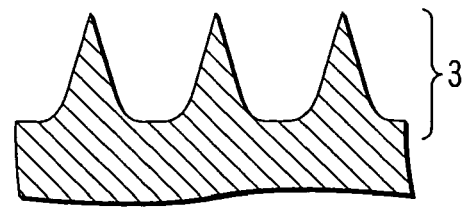
Figure 3:
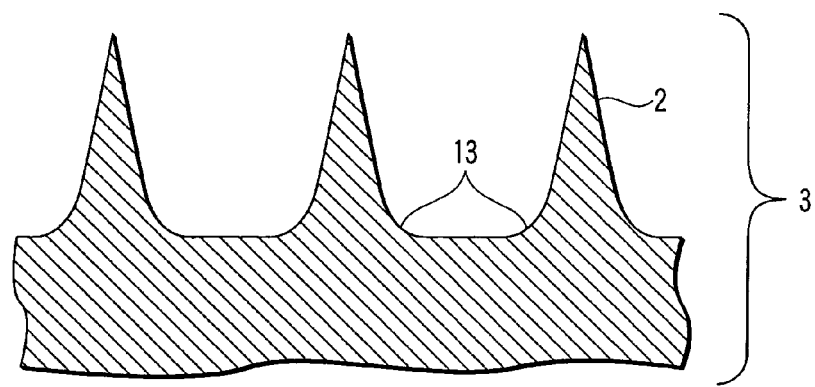
FIG. 3 shows a cross-sectional view of an example of a microneedle manufactured by the method according to the invention.

Other grooves are sequentially formed by the same method used for forming the first linear groove 22, and as shown in FIG. 2F, a substrate 3 having the needles 2 with an approximately triangular cross section on the surface is obtained by forming a desired number of the needles 2. The number of columns of the microneedle aligned into an array is determined by the number of the needles 2 formed in this step. As shown in FIG. 3, the cross sectional shape of the needle 2 has a slope of the sidewall corresponding to the inclined surface 7 formed at the tip of the dicing blade 11, and the portion where the side surface intersects the basal plane becomes to have a shape 13 with a slope corresponding to the chamfered surface 8 formed at the tip of the dicing blade 11 in FIG. 1B.

Figure 4:
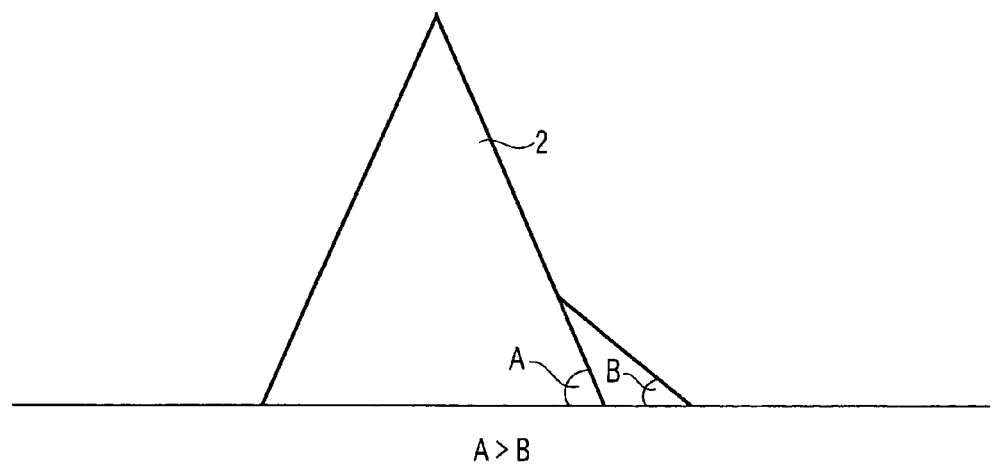
FIG. 4 shows a cross-sectional view of another example of a microneedle manufactured by the method according to the invention.

While the portion where the side surface intersects the basal plane has a circular slope in the cross section of the needle 2 in the example shown in FIG. 3, the stress converged at the base of the microneedle upon piercing may be relaxed by forming at least one auxiliary plane so that the intersection angle B between the auxiliary plane and basal plane is smaller than the intersection angle A between the side surface and basal plane as shown in FIG. 4. In this case, a dicing blade on which at least one auxiliary plane is used for processing the tip of the dicing blade 11 so as to chamfer the apex portion formed by intersection between the inclined surface 7 and tip surface 5 of the dicing blade.

<Process for Providing a Second Linear Groove>

Subsequently, second linear grooves are formed so as to intersect the first linear grooves. The second linear grooves may be formed under the same condition as forming the first linear grove 21 and first linear groove 22 by turning the substrate 3 on which the first linear grove 21 and first linear groove 22 are formed. The intersection angle between the first linear grooves and the second linear grooves is equal to the turning angle of the substrate 3.

Figure 5:
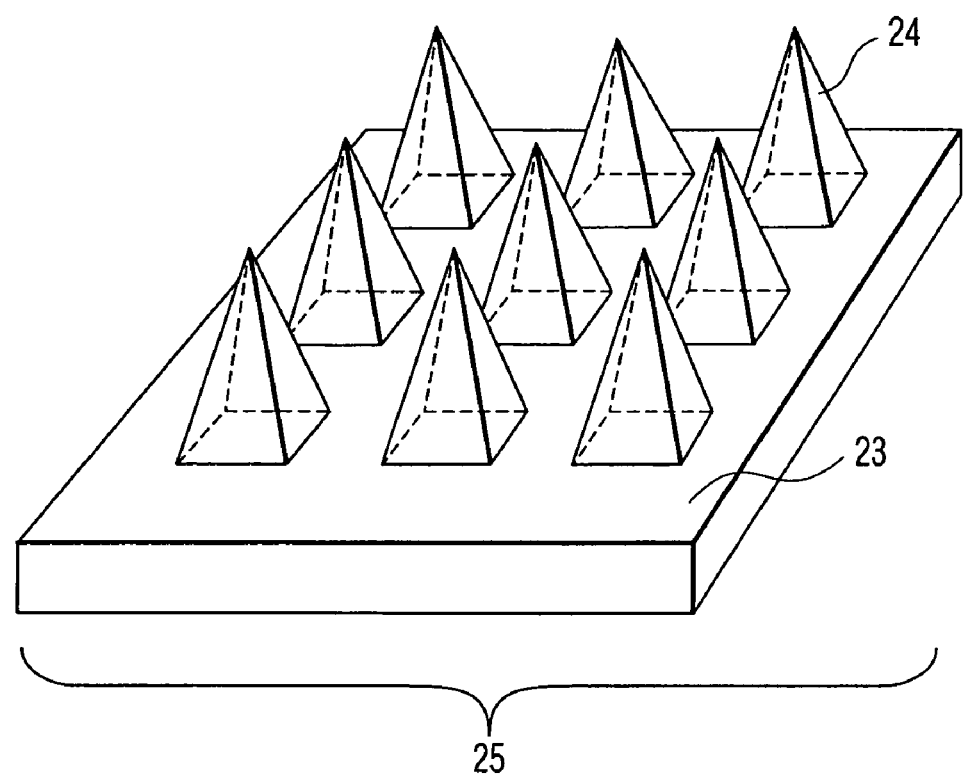
FIG. 5 shows a perspective view of a microneedle manufactured by the method according to the invention.

FIG. 5 is an example in which the substrate 3 on which the needles 2 are formed is turned by 90°, and the substrate is subjected to dicing under the same condition as forming the above-mentioned grooves. The portions left behind without being ground form an array of square cones 24 as shown in FIG. 5, and an array of microneedles 25 is obtained on a substrate 23. While the square cone 24 is joined to the substrate 23 with a sharp corner in FIG. 5, the base portion of the square cone may have a gentle slope by using the chamfered dicing blade 11 as described above.

The step for providing the second linear groove may be repeated several times. A cone shape microneedle having a variety of shapes of the basal plane may be manufactured by controlling the number of the dicings and the intersection angle between the grooves.

For example, a square cone having a rhombohedral basal plane may be obtained by providing a plurality of second linear grooves and shifting the angle of direction of second dicing by 60° from the angle of direction of first dicing. The point angles of the opposed corners of the rhombohedral basal plane are 60° and 120°, respectively.

A microneedle having a hexagonal cone shape may be obtained by forming a plurality of second linear grooves and a plurality of third linear grooves in addition to the first liner grooves and applying dicing in three directions.

Projected portions may be left behind in some cases around the microneedle group obtained. These projected portions may be removed by dicing, if necessary.

Cone shape microneedles having basal planes with a variety of polygonal shapes may be manufactured by controlling the cross sectional shape of the dicing blade, the number of applications of dicing and the intersection angle between the grooves. Since microneedles may be manufactured for every column by providing linear grooves, microneedles aligned in an array may be collectively formed.

<Linear Grooves Formed by Plural Times of Grinding in a Horizontal Direction>

Plural times of grinding may be applied by moving the dicing blade in a horizontal direction on the surface of the substrate relative to one linear groove for forming the liner grooves. Since the distance between the linear grooves may be controlled by the number of grinding by applying grinding plural times in the horizontal direction on the surface of the substrate, the pitch width between the manufactured microneedles may be controlled.

Figure 6A:
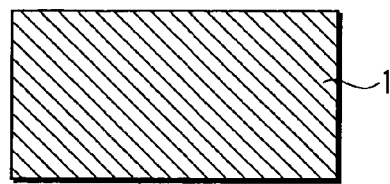
FIGS. 6A to 6D show cross-sectional views illustrating a method of manufacturing a microneedle in which linear grooves are formed by grinding plural times in the horizontal direction by the method according to the invention.
Figure 6B:
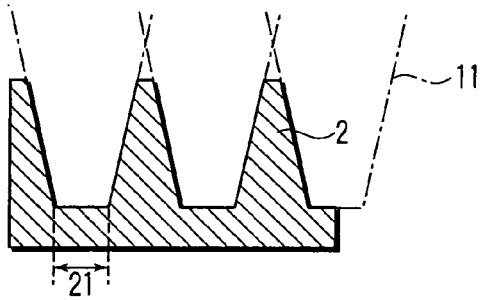
Figure 6C:
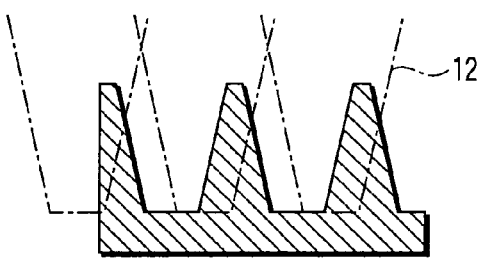
Figure 6D:
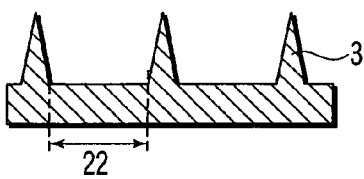

FIGS. 6A to 6D show a specific example of forming linear grooves by plural times of grinding in the horizontal direction. In FIG. 6B, reference numeral 11 shows a locus of the blade in first grinding, and reference numeral 21 shows the width of the flat portion at the top of the blade. In FIG. 6C, reference numeral 12 shows the locus of the blade in second grinding. In FIG. 6D, reference number 22 shows the distance between the needles.

<First Linear Groove and Second Linear Groove Sequentially Formed to One Another>

The first linear groove and second linear groove may be sequentially formed to one another when the first linear groove and second linear groove are formed. Sequentially forming the first linear groove and second linear groove to one another suppresses the mechanical strength of the substrate from being impaired when forming the grooves, suppresses the microneedles from being broken in the processing step, and microneedles excellent in form accuracy (in particular, form accuracy at the tip of the microneedle) can be manufactured.

Figure 7:
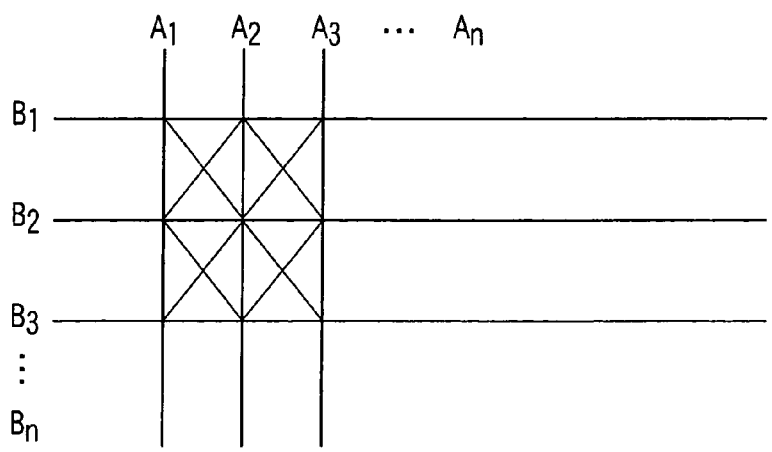
FIG. 7 shows a plane view illustrating a method of sequentially forming first linear grooves and second linear grooves by a method according to the invention.

FIG. 7 shows a specific example of sequentially forming the first linear groove and second linear groove to one another. FIG. 7 is an example when the first linear grooves A are formed in 1 to n columns (referred to $A_1$ to $A_n$ (n=1, 2, 3 and so on), respectively), the second linear grooves B are formed in 1 to n rows (referred to $B_1$ to $B_n$ (n=1, 2, 3 and so on), respectively), and the first linear grooves A intersect the second liner grooves B at an angle of 90° to form microneedles into a matrix of (n−1) columns×(n−1) rows. The first linear grooves A and second linear grooves B may be sequentially formed to one another under a rule of (1) forming $A_{n+1}$ immediately after forming $A_n$ is prohibited, and (2) forming $B_{n+1}$ immediately after forming $B_n$ is prohibited. For example, the grooves may be formed in the order of $A_1$, $B_1$, $A_2$, $B_2$ and so on, or in the order of $A_1$, $A_3$, $B_1$, $B_3$, $A_2$, $A_4$, $B_2$, $B_4$ and so on.

When third linear grooves C to N-th linear grooves α (N=1, 2, 3 and so on, α=A, B, C and so on) are further provided in addition to the first linear grooves A and second linear grooves B, forming $α_{n+1}$ grooves may be prohibited immediately after forming $α_n$ grooves.

When the microneedle manufactured is transcribed, the microneedle 25 is used as a master plate, a replication plate is formed from the master plate, and the replication plate is used for transcription molding. This permits the shape of the manufactured microneedle to be transcribed onto various materials. For example, a microneedle using a material that gives low burden to the body may be manufactured by transcribing the replication plate onto biocompatible materials (such as medical silicone resin, maltose, polylactic acid and dextran). Since many microneedles may be manufactured using the same replication plate by manufacturing the replication plate having a high mechanical strength, productivity may be enhanced with a low manufacturing cost.

<Microneedle Formed to have Hollow Portion>

Figure 8A:
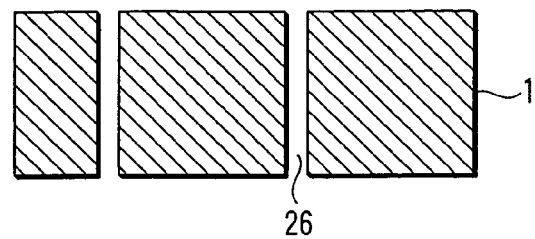
FIGS. 8A to 8F show cross-sectional views illustrating a method of manufacturing a microneedle according to the invention.
Figure 8B:
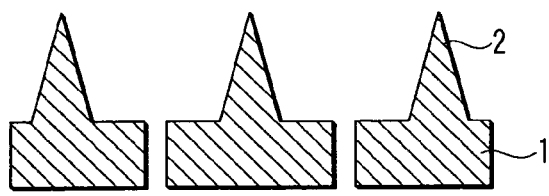
Figure 8C:
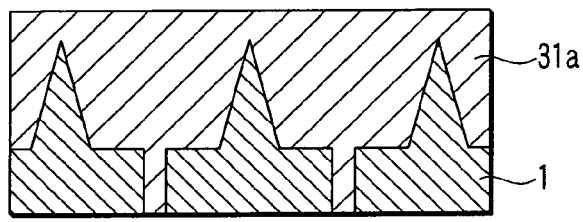
Figure 8D:
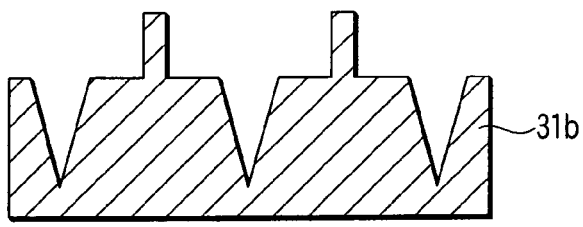
Figure 8E:
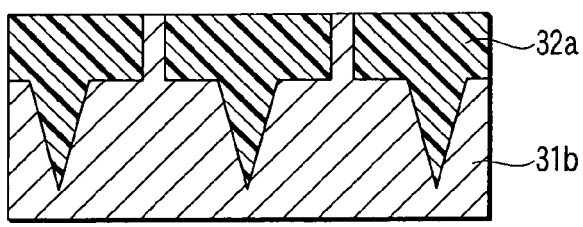
Figure 8F:
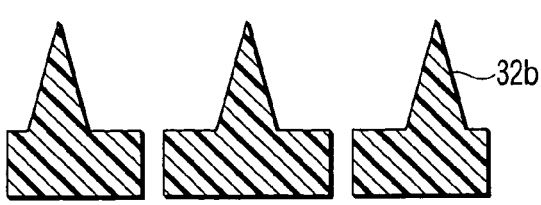

A penetrated hole is formed on the substrate 1 in advance, and the microneedle may be formed at a position displaced from the position of the penetrated hole. This method will be described with reference to FIGS. 8A to 8E. A penetrated hole 26 is formed on the substrate 1 (FIG. 8A), and the substrate is diced so as to form the needle 2 at a position displaced from the position of the penetrated hole 26 (FIG. 8B). A filler layer 31 is formed on the substrate 1 (FIG. 8C), and a replication plate 31b is formed by peeling the filler layer 31 from the substrate 1 (FIG. 8D). A microneedle material 32a is deposited on the replication plate 31b (FIG. 8E), and a microneedle 32b is formed by peeling the microneedle material 32a from the replication plate 31b (FIG. 8F).

Figure 9:
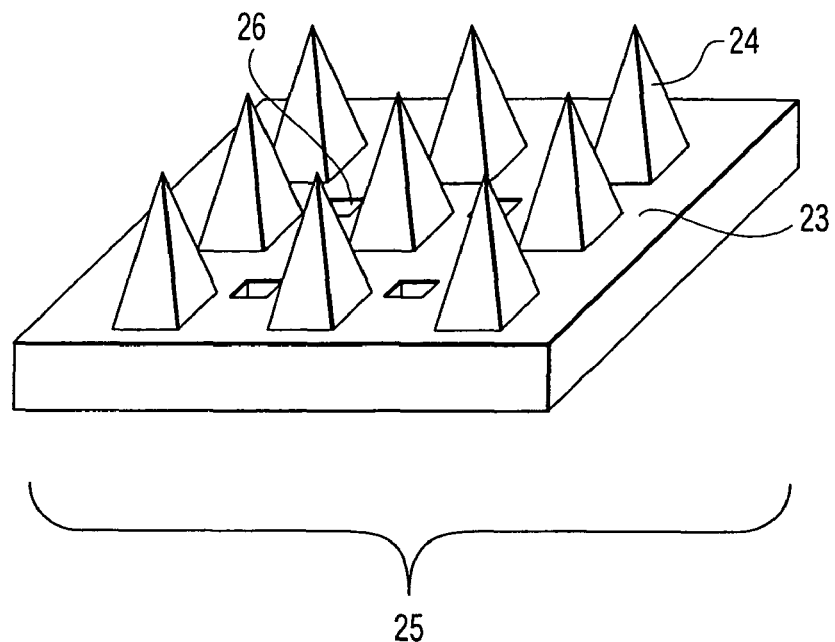
FIG. 9 shows a perspective view of a microneedle manufactured by the method according to the invention.

FIG. 9 shows a perspective view of the microneedle thus formed. As shown in FIG. 9, arrayed square cones 24 are formed on the substrate 23 with a penetrated hole 26 at the center of the space surrounded by the square cones 24, thus the microneedle array 25 is obtained.

Penetrated holes or non-penetrated holes are provided on the substrate, and the microneedle may be formed so as to overlap the position of the penetrated hole or non-penetrated hole. Examples of this method will be described with reference to FIGS. 10A and 10B, 11A and 11B, 12A and 12B, and 13A and 13B.

Figure 10A:
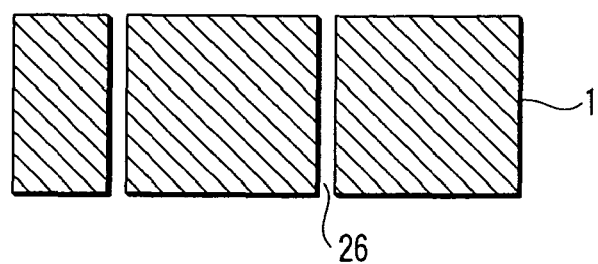
FIGS. 10A and 10B show cross-sectional views illustrating a method of manufacturing a microneedle according to the invention.
Figure 10B:
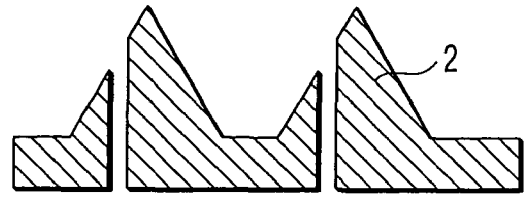

As shown in FIG. 10A, a penetrated hole 26 is formed on the substrate 1. As shown in FIG. 10B, the needle 2 is formed by dicing so as to form the needle 2 at a position that overlaps the position of the penetrated hole 26.

A non-penetrated hole 26 is formed on the substrate 1 in the example shown in FIG. 11A. Then, the needle 2 is formed by processing the substrate 1 as shown in FIG. 11B so that the hole is penetrated by dicing so as to form the needle 2 at a position that overlaps the position of the non-penetrated hole 26 on the surface of the substrate 1 opposed to the surface on which the non-penetrated 26 hole is formed.

A non-penetrated hole 26 is also formed on the substrate 1 in the example shown in FIG. 12A. Then, the needle 2 is formed by dicing to a depth smaller than the depth of the non-penetrated hole 26 so as to form the needle 2 at a position that overlaps the position of the non-penetrated hole 26 on the surface of the substrate 1 on which the non-penetrated hole 26 is provided as shown in FIG. 12B.

A non-penetrated hole 26 is also formed on the substrate 1 in the example shown in FIG. 13A. Then, the needle 2 is formed by dicing to a depth larger than the depth of the non-penetrated hole 26 so as to form the needle 2 at a position that overlaps the position of the non-penetrated hole 26 on the surface of the substrate 1 on which the non-penetrated hole 26 is provided as shown in FIG. 13B.

As shown in FIGS. 8A to 8F, 9, 10A and 10B, 11A and 11B, 12A and 12B, and 13A and 13B, the microneedle having the hollow portion may exhibit an effect that a drug solution is maintained in the hollow portion.

Another embodiment of the invention will be described below with reference to FIGS. 14A to 14G.

<Process for Forming an Island Structure by Forming Grooves on a Substrate (FIGS. 14A and 14B)>

Figure 15A:
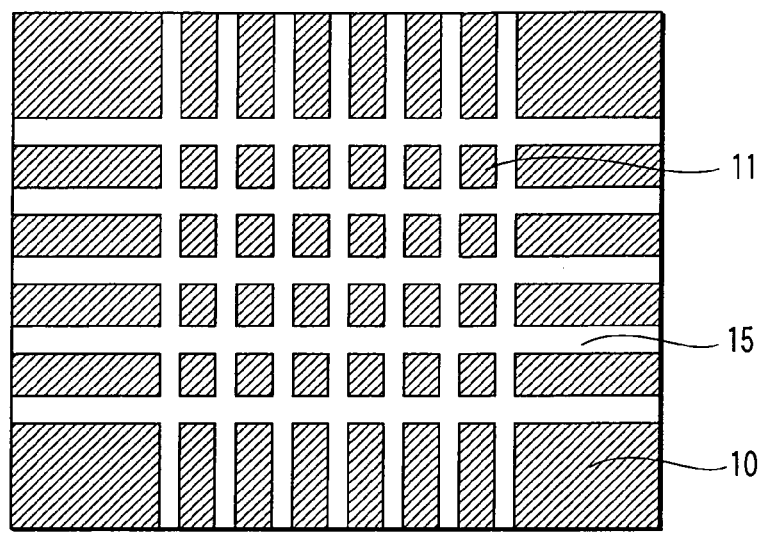
FIGS. 15A and 15B show plane views of examples of forming grooves.
Figure 15B:
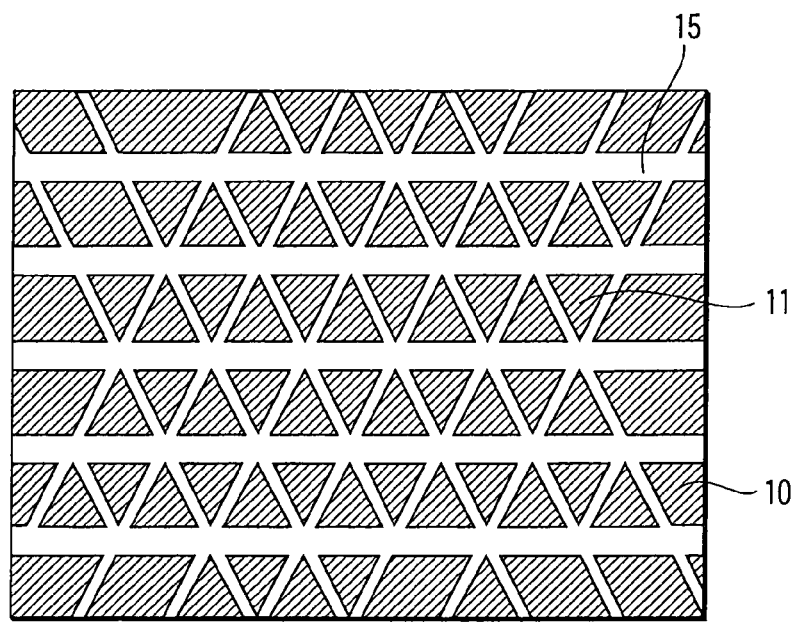

A substrate 10 is prepared, and grooves are formed thereon by grinding the substrate. Island structures 11 aligned in a checkerboard shape are thus formed. The checkerboard shape as used herein refers to a configuration in which figures closed by continuous straight lines or curved lines are aligned with a distance apart to one another. Examples of the configuration include squares aligned as shown in FIG. 15A, or triangles aligned as shown in FIG. 15B as well as aligned figures having an arbitrary number of apexes. The substrate is processed for every column by providing grooves on the substrate and by forming the island structures for every column. The microneedles may be manufactured collectively, and a structure in which the needles are aligned in an array may be readily formed.

The material may by appropriately selected depending on the processing method. Examples of the material of the substrate available include ceramics such as alumina, aluminum nitride and machinable ceramics; crystalline materials such as silicon, silicon carbide and quartz; organic materials such as acrylic resins and polyacetal; metallic materials such as nickel and aluminum; and glass.

When dicing is used for grinding, the taper angle of the microneedle manufactured may be controlled by changing the angle of the inclined surface of the dicing blade.

When the grooves are formed by dicing, the dicing blade may be changed to another dicing blade having a different inclined surface for every groove. This permits the taper angle of the side surface of the groove to be different for every groove. Consequently, the taper angle of the microneedle manufactured may be different for each side surface, and a microneedle having a bilateral asymmetric shape may be designed and manufactured.

Figure 16A:
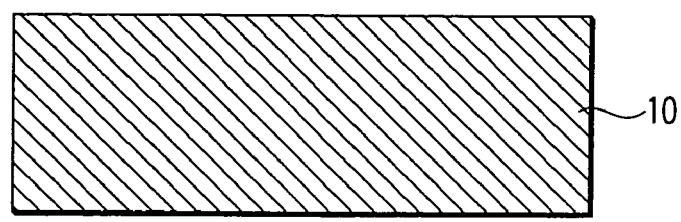
FIGS. 16A to 16C show cross-sectional views illustrating a method of forming a multistage structure by repeatedly forming the grooves.
Figure 16B:
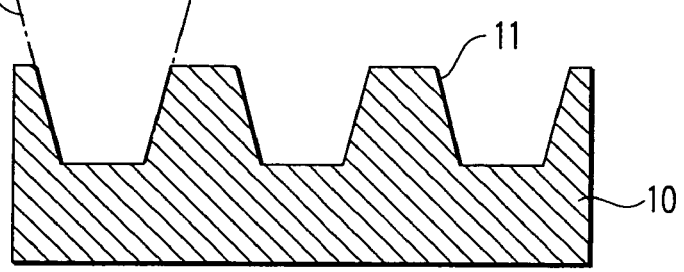
Figure 16C:
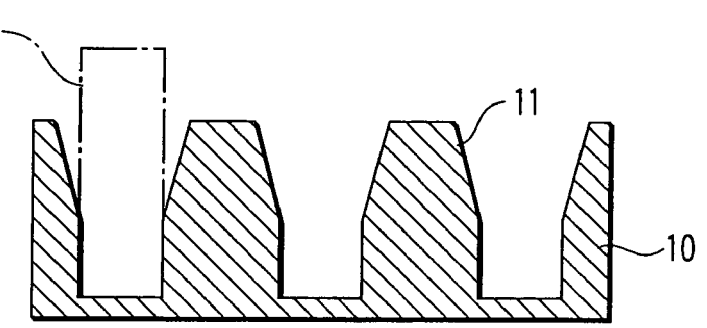

As shown in FIGS. 16A to 16C, a first stage groove is formed with a blade 16, and then the first stage groove may be processed again by tracing the groove with a blade 17 to thereby form a second stage groove. This processing using the dicing blade 17 having the vertical inclined surface permits a microneedle having a side surface including a vertical surface and a high aspect ratio to be manufactured.

The taper angle of the side surface of the microneedle manufactured may be changed gradually by changing the inclined surface of the dicing blade for each dicing step in forming the first stage groove and second stage groove. A microneedle having a reinforced shape at the bottom that receives high stress upon piercing may be manufactured, for example, by reducing the taper angle at the bottom of the microneedle. This permits a microneedle that is hardly broken upon piercing to be designed and manufactured.

Grooves at the third stage and thereafter may be formed by changing the dicing blade to another dicing blade having a different inclined surface as in forming the second stage groove, and the third stage grooves may be formed by repeating re-processing to trace the groove. This permits microneedles having various taper angles to be designed and manufactured.

Figure 17A:
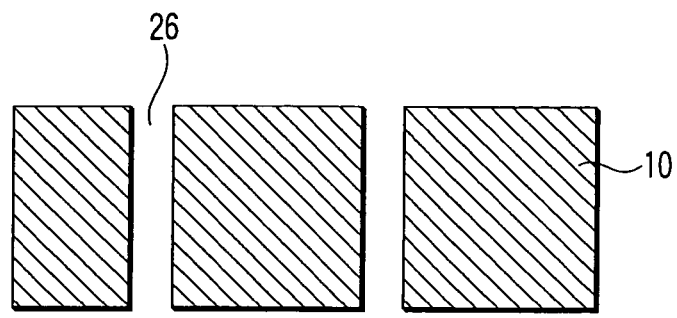
FIGS. 17A to 17C show cross-sectional views illustrating a method of forming a multistage structure by repeatedly forming the grooves.
Figure 17B:
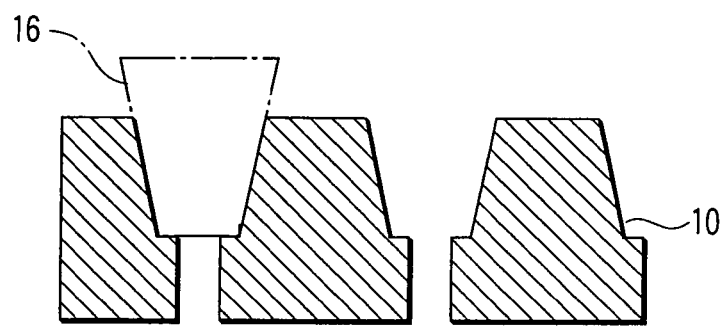
Figure 17C:
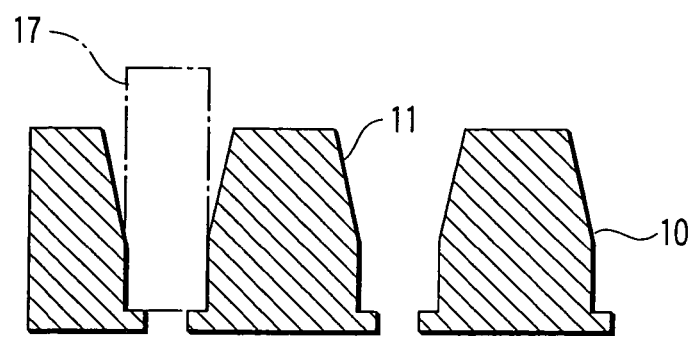

As shown in FIGS. 17A to 17C, a penetrated hole 26 is formed on the substrate 10 in advance, the first stage groove is formed, and then the second stage groove is formed by re-processing to trace the first stage groove.

<Process for Forming a Master Plate of the Microneedle by Subjecting the Island Structure to Isotropic Etching (FIG. 14C)>

The substrate 10 on which the island structure 11 is formed is subjected to isotropic etching. "Isotropic etching" as used herein is defined to include not only perfect isotropic etching, but also etching under dominantly isotropic etching tendency with a slight tendency of anisotropy. The tip of the microneedle may be sharpened without being limited by crystal orientation of the substrate by applying isotropic etching. The method for isotropic etching is not particularly limited, and methods using a dry etching apparatus by, for example, RIE, magnetron RIE, ECR, ICP, NLD, microwave and helicon wave discharge may be used. Dry etching using a gas such as $XeF_2$ may also be used.

The entire island structure is contracted by a given distance as shown in FIG. 18B by subjecting the needle as shown in FIG. 18A to isotropic etching. Consequently, the base of the needle is rounded as shown in FIG. 18C while the tip of the needle is sharpened. The needle may have a shape that is easy for piercing and is hardly broken by adjusting the shape of the needle by subjecting the needle to isotropic etching.

Freedom of design of the shape, taper angle and size may be enhanced by subjecting the needle to isotropic etching after forming the island structure, and the tip of the microneedle may be sharpened without limiting the substrate to crystalline materials.

<Process for Manufacturing a Replication Plate from the Microneedle (FIGS. 14D and 14E)>

A filler layer 13a is formed on the microneedle 12 formed by the above-mentioned method, and a recessed replication plate 13b is formed by peeling the filler layer 13a from the microneedle 12. Since a lot of microneedles may be manufactured from the same replication plate 13a by manufacturing an integrated replication plate having a high mechanical strength, the production cost is reduced while productivity is enhanced.

The material of the filler layer is not particularly limited, and the material may be selected in terms of shape adapability enough for functioning as the replication plate, transcribing ability in the transcription molding to be described below, durability and releasing ability. For example, nickel and thermosetting silicone resin may be used for the filler layer. The method for forming the filler layer includes plating, PVD and CVD when nickel is selected for the material.

The method for peeling the filler layer from the microneedle 12 available includes peeling by a physical peeling force and selective etching.

Subsequently, the replication plate 13b is filled with a microneedle material 14. While the material of the microneedle is not particularly limited, microneedles applicable for the living body may be formed by using biocompatible materials such as medical silicone resins, maltose, polylactic acid, dextran and polysaccharide. The microneedle becomes harmless to the body by using the biocompatible material even when the microneedle is broken and left behind in the body. While the method for filling the microneedle material is not particularly limited, imprinting, hot embossing, injection molding, extruding and casting may be favorably used in terms of productivity.

The microneedle material is peeled from the replication plate to obtain a microneedle 14 by transcription molding.

A releasing layer for enhancing releasing effect may be formed on the surface of the replication plate before filling the microneedle material in order to improve peelability of the replication plate (not shown). Widely known fluorinated resins may be used for the releasing layer. A method for forming a thin film such as PVD, CVD, spin-coating and dip-coating may be favorably used for forming the releasing layer.

The method of manufacturing the microneedle of the invention may be implemented as described above. However, the method of manufacturing the microneedle of the invention is not limited to the above-mentioned embodiments, and other known method that may be inferred in each step may be included.

Figure 19A:
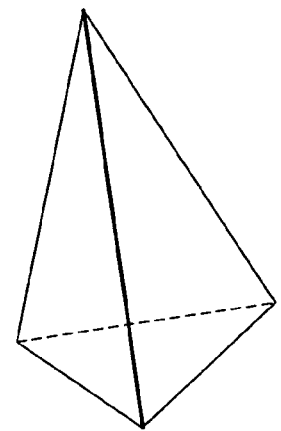
FIGS. 19A to 19C show perspective views of microneedles manufactured by a method according to the invention.
Figure 19B:
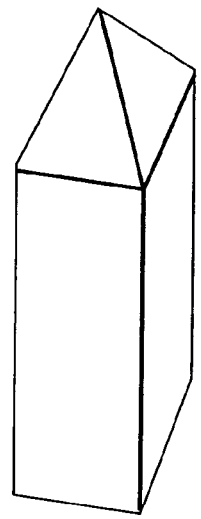
Figure 19C:
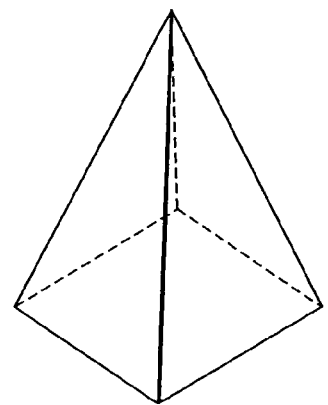

Microneedles of various shapes may be designed and manufactured by controlling the taper angle of the groove formed in the method of manufacturing the microneedle of the invention. For example, a shape in which a ridge formed by connecting one apex of a triangular basal plane and the apex at the tip is approximately vertical (FIG. 19A) may be designed when grooves are formed in three directions and when the taper angle of the side surface of the groove in one direction of the three directions is made to be different from the taper angles of the other side surfaces of the groove in the other two directions. A shape having a square basal plane, vertical side surfaces and a square cone tip may be formed (FIG. 19B) by forming the grooves in two directions and by changing the taper angle halfway of the depth of each groove. A square cone shape having a rectangular basal plane may be designed (FIG. 19C) by forming the grooves in two directions so as to permit one groove to intersect the other at an angle of 90°. However, it is needles to say that the microneedle manufactured by the method of manufacturing the microneedle of the invention is not limited to these shapes.

EXAMPLE 1

The invention will be described in detail by way of specific examples. FIGS. 2A to 2F show partial cross-sectional views of an embodiment of the invention.

The tip of a dicing blade containing diamond abrasive grains was processed into a desired shape to be described below by grinding with a diamond grinding stone. FIGS. 1A and 1B show partial cross-sectional views of a tip of the disk-shaped dicing blade. As shown in FIG. 1A, the shape of the dicing blade 12 before grinding has an intersection angle of 90° between the side surface 4 and tip surface 5 to form the apex 6. The dicing blade 12 was processed using a diamond grinding stone to obtain a dicing blade 11. As shown in FIG. 2B, the dicing blade 11 has an inclined surface 7, and the tip portion formed by intersection between the inclined surface 7 and tip surface 5 was processed into a shape having a chamfered surface 8. The tip of the dicing blade was subjected to grinding in this example using a dicing blade with a thickness of 1 mm so that the tip surface 5 has a width of 200 μm and the angle between the side surface 4 and inclined surface 7 is 160°. The inclination angle of the inclined surface 7 determines the angle of the sidewall of the finally formed microneedle. The chamfered surface 8 determines the shape of the bottom portion of the finally formed microneedle. The inclination angle of the inclined surface 7 at the tip of the dicing blade in this example was selected to be 160° in order to adjust the tip angle of the finally formed square cone microneedle to 40°.

Subsequently, a first linear groove was formed on the surface of an alumina substrate 1 by dicing with the dicing blade 11 having the tip processed as described above. The alumina substrate 1 with a size of 30 mm square and a thickness of 3 mm was prepared as shown in FIG. 2A. Then, a groove with a length of 30 mm was formed by dicing the surface of the alumina substrate 1 to a depth of 300 μm as shown in FIG. 2B while the dicing blade 11 is rotated.

The first linear groove 21 was formed as shown in FIG. 2C by dicing as described above. The first linear groove 21 had a width of about 418 μm at the upper opening and a depth of 300 μm. The inclination angle of the sidewall of first linear groove 21 corresponds to the inclination angle of the inclined surface 7 formed at the tip of the dicing blade 11 shown in FIG. 1B, and the angle between the surface of the alumina substrate 1 and the sidewall of the first linear grove 21 was 110° in this example. Likewise, the portion where the sidewall of the first linear grove 21 intersects the bottom had a shape with a slope corresponding to the chamfered surface 8 formed at the tip of the dicing blade 11 as shown in FIG. 1B.

Subsequently, an adjoining first linear groove 22 was formed on the surface of the substrate 1. As shown in FIG. 2D, a groove was formed adjacent to the first linear groove 21 with the dicing blade 11 under the same condition as forming the first linear groove 21. The groove was formed with the dicing blade 11 so that the first linear groove 22 overlaps the first linear groove 21 with a width of 100 μm. The groove was ground parallel to the first linear groove 21. As a result, another first linear groove 22 with a depth of 300 μm and a length of 3 mm was formed adjacent to the first linear groove 21. A needle 2 having a sharp tip was formed between the first linear groove 21 and another first linear groove 22.

The height of the needle 2 is determined by the depth of dicing, the angle of the inclined surface 7 at the tip of the dicing blade 11, and an overlap length between the first linear groove 21 and another first linear groove 22. The height of the needle 2 and the width at the root of the needle 2 were about 162 μm and 118 μm, respectively, in this example. The tip of the needle 2 formed by overlap of the inclined surfaces 7 at the tip of the dicing blade had a point angle of 40°.

Then, grooves were sequentially formed as forming the first linear groove 22, and a substrate 3 on the surface of which needles 2 having an approximately triangular cross section were formed was obtained by forming a desired number of the needles 2 as shown in FIG. 2F. Six grooves in total were formed in this example, and five needles 2 were formed by forming the six grooves. As shown in FIG. 3, the cross section of the needle 2 has an inclined sidewall that matches the inclined surface 7 formed at the tip of the dicing blade 11. The portion where the side surface intersects the basal plane has a shape 13 with a slope corresponding to the chamfered surface 8 formed at the tip of the dicing blade 11 shown in FIG. 1B.

Subsequently, the substrate 3 on the surface of which five needles 2 were formed by the above-mentioned step for forming six grooves was turned by 90°, and grooves were formed by dicing under the same condition as in the step for forming the grooves. Consequently, five second linear grooves were formed, and the portion left behind without being ground becomes an array of square cones 24 as shown in FIG. 5, and microneedles 25 aligned in an array were obtained on the substrate 23. The microneedles 25 aligned into an array of 5 columns and 5 rows were obtained in this example. The microneedle obtained had a square cone shape with a point angle of 40°, a height of about 162 μm and a width of one side of the basal plane of 118 μm.

EXAMPLE 2

A replication plate was manufactured from a master plate using the microneedle 25 as the master plate for replication of the microneedle manufactured, and the replication plate was subjected to transcription molding. A nickel film with a thickness of 600 μm was formed by plating on the surface of the microneedle 25. Then, the nickel film was peeled from the microneedle 25 to manufacture a replication plate, which was then transcribed onto polylactic acid by imprinting to obtain a microneedle made of polylactic acid.

EXAMPLE 3

A single crystalline silicon substrate with a thickness of 525 μm was prepared as a substrate.

Then, the silicon substrate was subjected to dicing into a checkerboard pattern using a dicing blade having an inclined angle of 170° between the side surface and inclined surface. The top plane of the island structure formed by processing was a square having a length of one side of 100 μm. The processing depth was 250 μm.

The island structure formed was then subjected to isotropic etching. ICP-RIE was used for isotropic etching, and the reaction gas used was $SF_6$. The island structure was etched until the top plane became a point.

A square cone microneedle with a size at the root of 100 μm, a height of 250 μm, a point angle of 20° and a tip diameter of 100 nm was formed.

EXAMPLE 4

A single crystalline silicon substrate with a thickness of 525 μm was prepared as a substrate (FIG. 16A).

The silicon substrate was subjected to dicing into a checkerboard pattern using a dicing blade 16 having an inclined angle of 165° between the side surface and inclined surface (FIG. 16B). The top plane of the island structure formed by dicing was a square with a side length of 70 μm, and the processing depth was 150 μm.

Then, the same processed portion as above of the substrate was subjected to dicing using a dicing blade 17 having an inclined angle of 90° (FIG. 16B). The processing depth was 150 μm.

Then, the island structure formed was subjected to isotropic etching. ICP-RIE was used for isotropic etching, and $SF_6$ gas was used as a reaction gas. The island structure was etched until the top plane became a point.

The microneedle formed under the above-mentioned conditions had a height of the tapered portion at the tip of 150 μm, a height of the perpendicular portion at the bottom side of 150 μm, a point angle of 30°, and a tip diameter of 100 nm.

EXAMPLE 5

A replication plate was formed by using the microneedle manufactured in Example 3 as a template, and the replication plate was used for transcription molding. A nickel film was formed on the microneedle as a filler layer by electroforming. Nickel sulfamate solution was used for the plating bath. The filler layer was formed by plating at a bath temperature of 45° C. for 5 hours using a 60% solution of nickel sulfamate. Then, the silicon microneedle as a template was dissolved at 80° C. for 4 hours using a 25% aqueous KOH solution to manufacture a replication plate.

Subsequently, the microneedle was manufactured by hot pressing using the replication plate. Polylactic acid as a biocompatible material was used as the microneedle material to be filled.

Consequently, a square cone microneedle made of polylactic acid was manufactured with a size at the root of 100 μm, a height of 250 μm, a point angle of 20° and a tip diameter of 100 nm.

The method of manufacturing a microneedle of the invention is applicable in the medical field as well as in various fields that require the microneedle, and is useful as the method of manufacturing the microneedle used for MEMS devices, development of new drugs and cosmetics.

What is claimed is:

1. A method of manufacturing a microneedle comprising the steps of:
   forming a plurality of first linear grooves on a substrate in parallel to one another along a first direction using grinding;
   forming a plurality of second linear grooves on the substrate in parallel to one another in a second direction intersecting the first direction using grinding, thereby forming an island structure having a top plane; and
   subjecting the island structure to isotropic etching, wherein the grinding uses a dicing blade, and wherein the dicing blade includes a side surface, a tip surface and an inclined surface therebetween, and a boundary between the inclined surface and tip surface is chamfered.

2. The method according to claim 1, further comprising:

using the microneedle manufactured by the method of manufacturing a microneedle according to claim 1 as a master plate;

forming a replication plate from the master plate; and manufacturing a microneedle by transcription from the replication plate.

3. The method according to claim 2, wherein the replication plate is transcribed onto a biocompatible material.

4. A microneedle comprising:

a substrate; and a plurality of arrayed needles supported on the substrate, wherein grooves between the needles have a configuration in which three groups of parallel linear grooves extending to three directions intersect with each other at an angle of 120 degrees, and wherein the needles have a shape that three sidewalls are joined with each other in a line to form a three-sided pyramid.

5. The microneedle according to claim 4, wherein the needles are made of a biocompatible material.

6. The microneedle according to claim 4, wherein the substrate has a non-penetrated hole or a penetrated hole.

7. The microneedle according to claim 4, wherein the needles have a non-penetrated hole or a penetrated hole.

* * * * *